(12) United States Patent
Bernhard, Jr. et al.

(10) Patent No.: US 7,634,919 B2
(45) Date of Patent: Dec. 22, 2009

(54) COOLER FOR TRANSPORTING AN ANIMAL CARCASS

(76) Inventors: Felix T. Bernhard, Jr., 407 N. Orange St., Louise, TX (US) 77455; Robert J. Popp, 898 N. FM 647, Louise, TX (US) 77455

( * ) Notice: Subject to any disclaimer, the term of this patent is extended or adjusted under 35 U.S.C. 154(b) by 566 days.

(21) Appl. No.: 11/189,494

(22) Filed: Jul. 26, 2005

(65) Prior Publication Data
US 2007/0022775 A1  Feb. 1, 2007

(51) Int. Cl.
*F25D 3/08* (2006.01)
(52) U.S. Cl. .................................. 62/371; 62/457.2
(58) Field of Classification Search .................. 62/371, 62/530, 457.2
See application file for complete search history.

(56) References Cited
U.S. PATENT DOCUMENTS

| 5,237,838 | A | * | 8/1993 | Merritt-Munson | ......... 62/457.2 |
| 5,336,124 | A | * | 8/1994 | Garside | ...................... 452/125 |
| 6,253,569 | B1 | * | 7/2001 | Hall | .......................... 62/457.2 |

* cited by examiner

*Primary Examiner*—Melvin Jones
(74) *Attorney, Agent, or Firm*—Keaty Law Firm

(57) ABSTRACT

A soft, insulating cooler with a detachable strap for transporting and/or storing head and cape of a dead animal, for instance deer. A hinged lid is closable by a pair of overlapping zippers. A pair of openings are formed in the lid to allow antlers to extend therethrough. A tightening cord is positioned about the openings to tighten the openings around the antlers and preserve the temperature inside the cooler. The inside of the cooler contains pouches for ice of other cooling medium. The outside of the cooler carries a pouch or pouches to transport small items.

10 Claims, 6 Drawing Sheets

COOLER FOR TRANSPORTING AN ANIMAL CARCASS

BACKGROUND OF THE INVENTION

The present invention relates to a cooler, and, more specifically, to a cooler used to transport and preserve a deer head and hide after harvesting.

When a hunter kills a large buck, he often wishes to keep the buck head and hide and have them mounted by a taxidermist. After harvesting the buck, the hunter must transport the head and hide from the hunting location preferably in a "fresh" condition so as not to damage the head and antlers during transportation. The head and hide must remain cool in order to preserve the deer for mounting.

Naturally, the large and irregular shape of the antlers presents a special problem. Conventional units are used to cool and transport the whole animal. They are designed to preserve the meat of the animal for consumption. These are not successful at preserving the head and hide for mounting purposes, nor do they protect the antlers or horns of game animals.

Various solutions were offered to solve the problem. One of such solutions is shown in U.S. Pat. No. 6,510,705, which discloses a portable ice chest with a soft top that can be used to cool and transport the head and hide of a deer. This device has hard sides and a hard bottom which make it unwieldy, heavy, and impractical to carry into a hunt.

The present invention contemplates provision of a cooler that is convenient and lightweight for transportation to and from the hunting location and is configured for transporting head and hide of the dead wild animal.

SUMMARY OF THE INVENTION

It is, therefore an object of the present invention to provide a lightweight, easily transportable cooler which is configured for temporary housing a carcass of a dead wild animal.

It is another object of the present invention to provide a cooler that is particularly adapted for transporting a head and antlers of a deer.

It is a further object of the present invention to provide a container with side compartments for accommodating small articles conventionally used during a hunt.

It is still a further object of the present invention to provide a cooler that is formed from flexible material that can be collapsed and transported to the site in the collapsed state.

These and other objects of the invention are achieved through a provision of a flexible deformable body formed from an insulated material, the exterior surface of which may carry camouflaged pattern. The flexible body has interior walls, which are provided with pouches for retaining ice packs therein to protect the animal head and cape during transportation. A flexible lid is secured to the upper edges of the walls. The lid has a closing means, which comprise a pair of partially overlapping zippers to further secure the open top of the cooler body.

One or more openings are formed in the lid to allow an animal part, for instance deer antlers, to extend therethrough. A tightening cord is secured around each opening, allowing the user to tighten the opening around the antlers. A pair of reinforcing flaps is secured adjacent to the zippers to protect the closure. One or more pockets are attached to exterior of the cooler body for receiving and retaining small items used in camping, hunting and the like. A handle is attached to opposing side walls of the cooler body to facilitate transportation of the cooler and its contents.

BRIEF DESCRIPTION OF THE DRAWINGS

Reference will now be made to the drawings, wherein like parts are designated by like numerals, and wherein.

DETAILED DESCRIPTION OF THE PREFERRED EMBODIMENT

Figure 1:
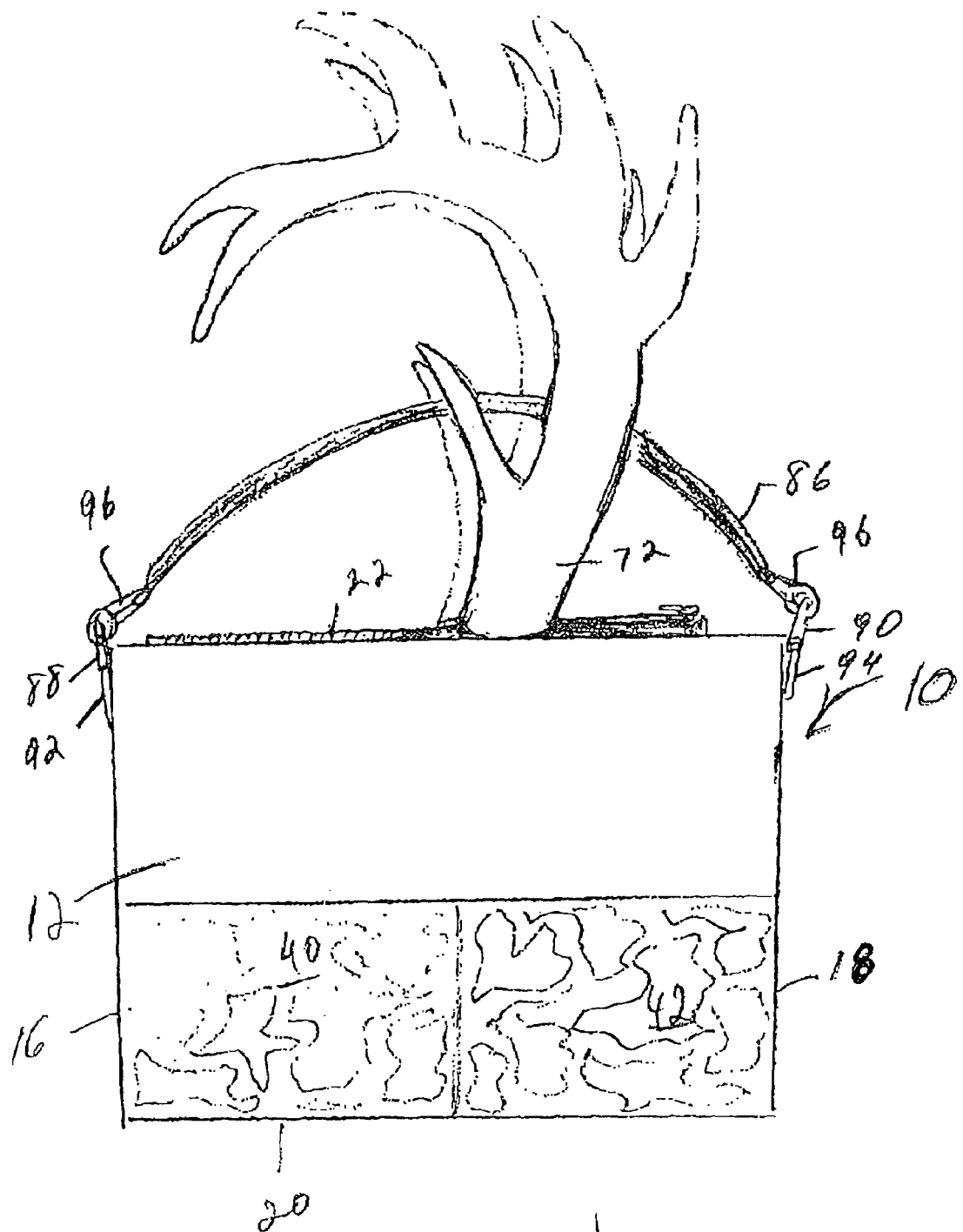
FIG. 1 is a side view of the cooler with the strap attached and antlers protruding through specially made openings in the top.
Figure 2:
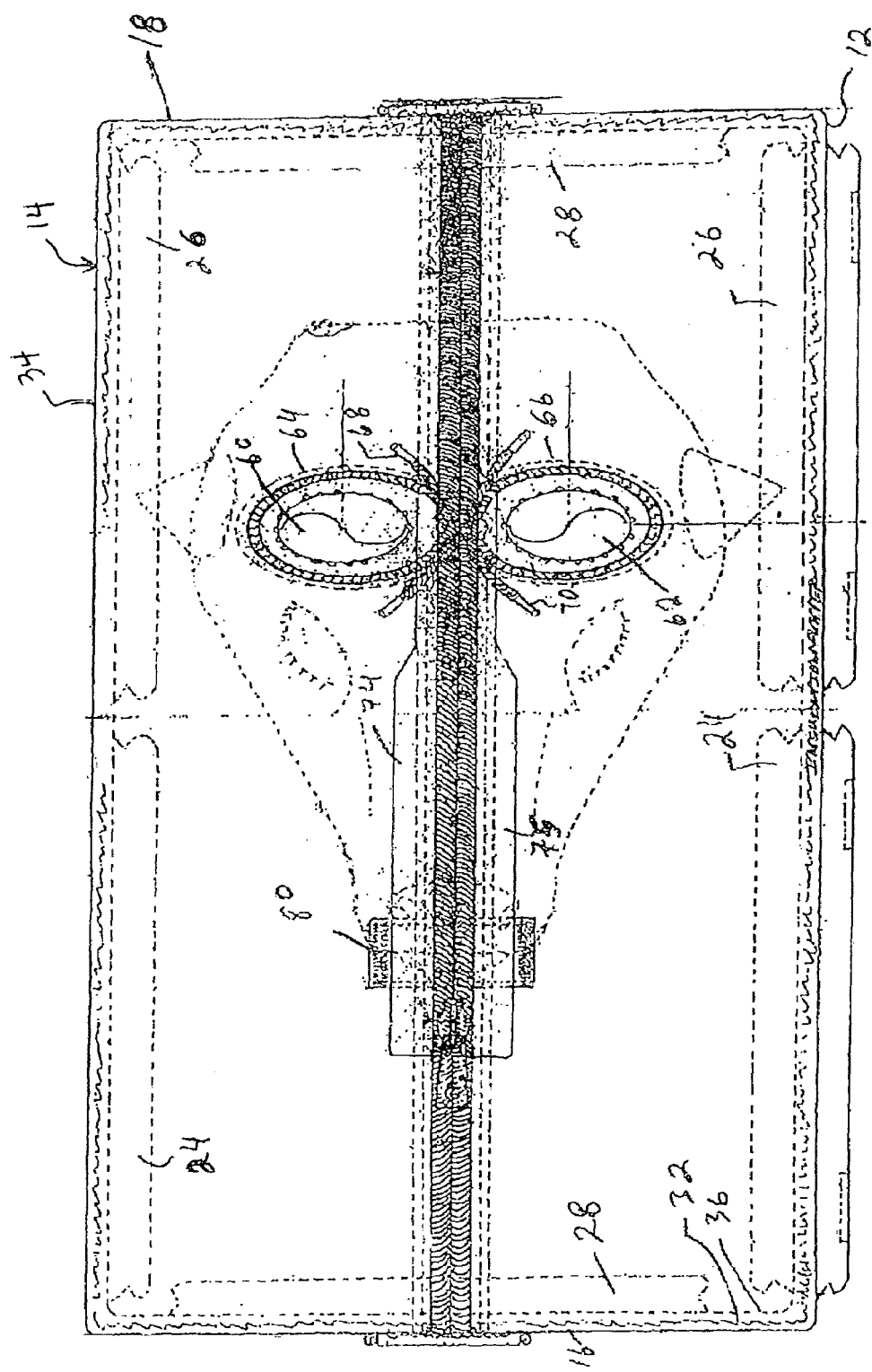
FIG. 2 is a plan view of the cooler showing position of the head of the dead animal in phantom lines.

Turning now to the drawings in more detail the soft-sided collapsible cooler of the present invention is generally designated by numeral 10. As can be seen in the drawings, the cooler is generally configured as a box-like enclosure having a front wall 12, a back wall 14, a first end wall 16 and a second end wall 18. The cooler 10 further comprises a closed bottom 20 and a closable top 22. The walls 12, 14, 16, 18, as well as the bottom 20 and top 22 are made from flexible collapsible material having waterproof outer and inner surfaces. The walls, the bottom and the top are formed from an insulated material to protect the contents of the cooler. An insulating layer 32 extends between an outside layer 34 and the inside layer 36 along the bottom, walls and top of the cooler 10.

Figure 6:
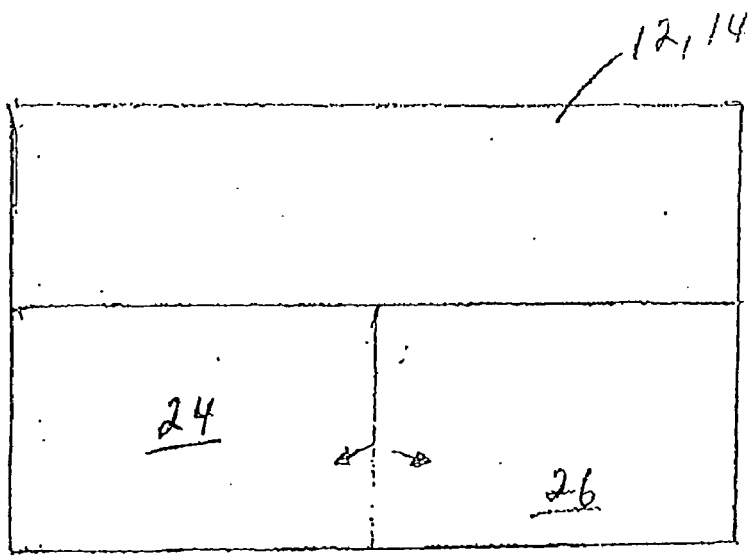
FIG. 6 is a plan view of a front inside wall showing a pair of compartments. The inside back wall similarly has a pair of inner compartments.
Figure 7:
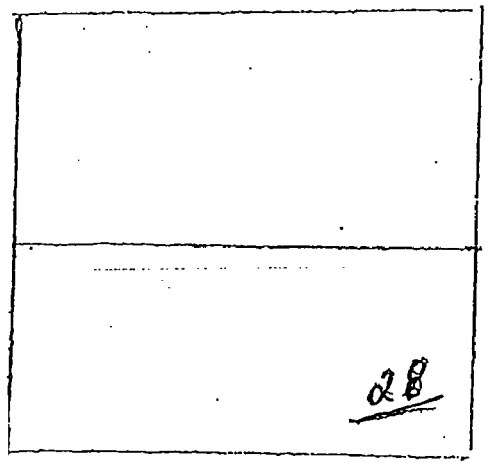
FIG. 7 is a plan view of the inside end wall showing an inner compartment.
Figure 8:
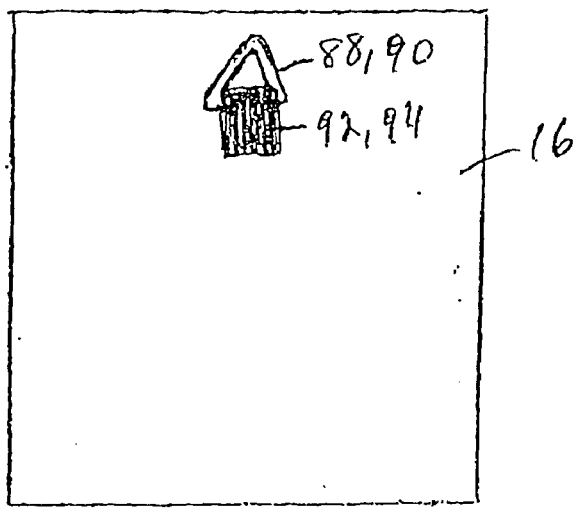
FIG. 8 is a plan view of the end wall showing a delta ring for attaching of a strap.
Figure 9:
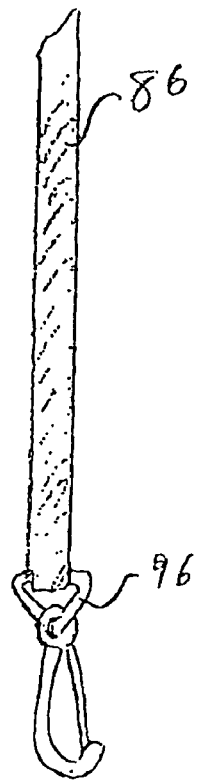
FIG. 9 is a detail perspective view showing a buckle on one end of the strap.

The walls 12, 14, 16, 18, the bottom 20 and the top 22 are secured together to form a main chamber 30, which is preferably large enough to accommodate a head and hide of a dead animal, or a carcass of a dead animal. The inside walls of the cooler are provided with a plurality of compartment, wherein a cooling medium, for instance "blue ice," dry ice or bags with ice, can be positioned. As can be seen in FIGS. 6 and 7, the front wall 12 and the back wall 14 are provided with two such compartments 24, 26. Each end wall 16 and 18 can be provided with one such compartment 28. Of course, any desired number of inner compartments can be made on the inside walls of the cooler 10, depending on the size and particular configuration of the inner chamber 30.

Figure 4:
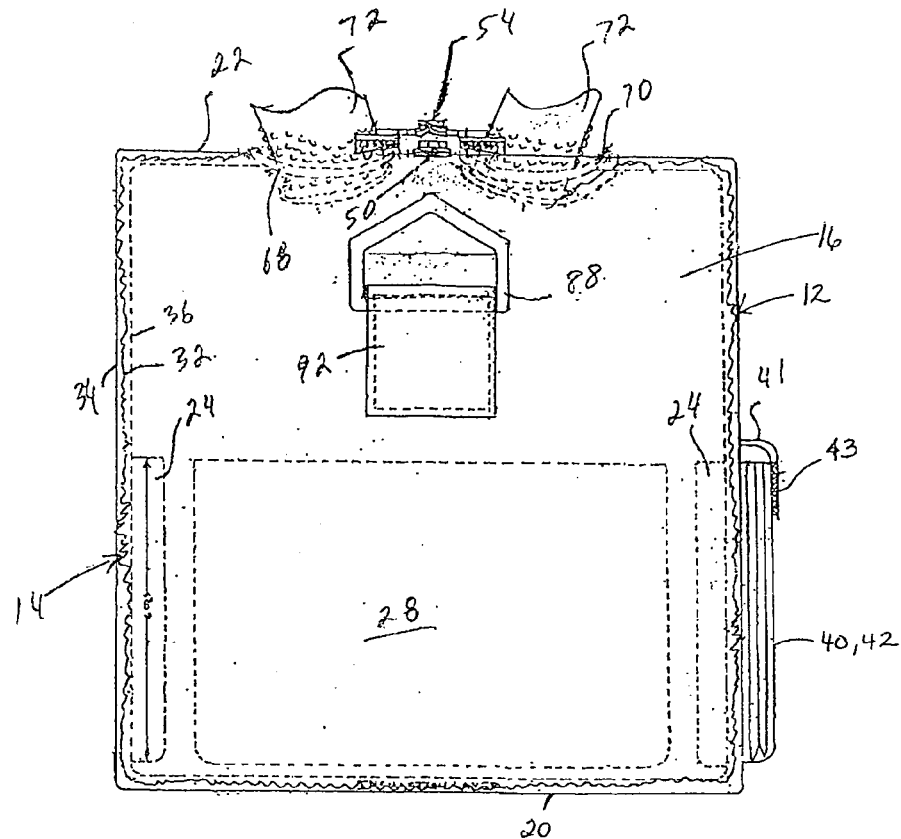
FIG. 4 is an end view of the cooler.
Figure 5:
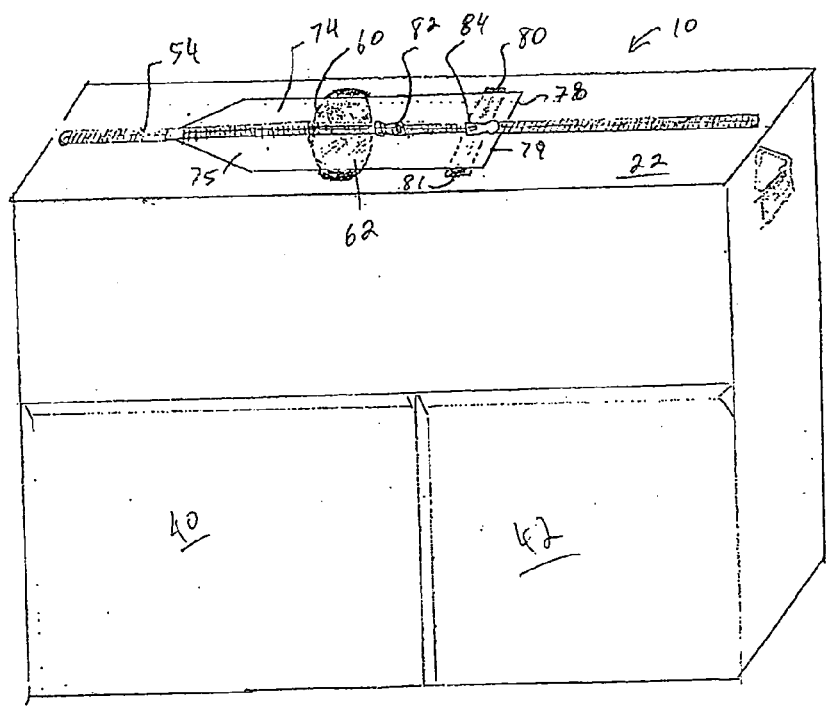
FIG. 5 is a perspective view of the cooler with a strap detached.

The outside of the front wall 12 of the cooler 10 is further provided with one or more outside compartments, or pouches 40, 42. Small items, such as tags, pens, hunting license, hunting accessories and the like can be positioned in the outside pouches 40, 42. A fold-down flap 41 (FIG. 4) can be secured to the front wall 12 to close the open top ends of the pouches 40, 42. If desired, marching hook and loop fastening strips 43 can be used to secure the bottoms of the flaps 41 to the exterior of the pouches 40, 42.

Figure 3:
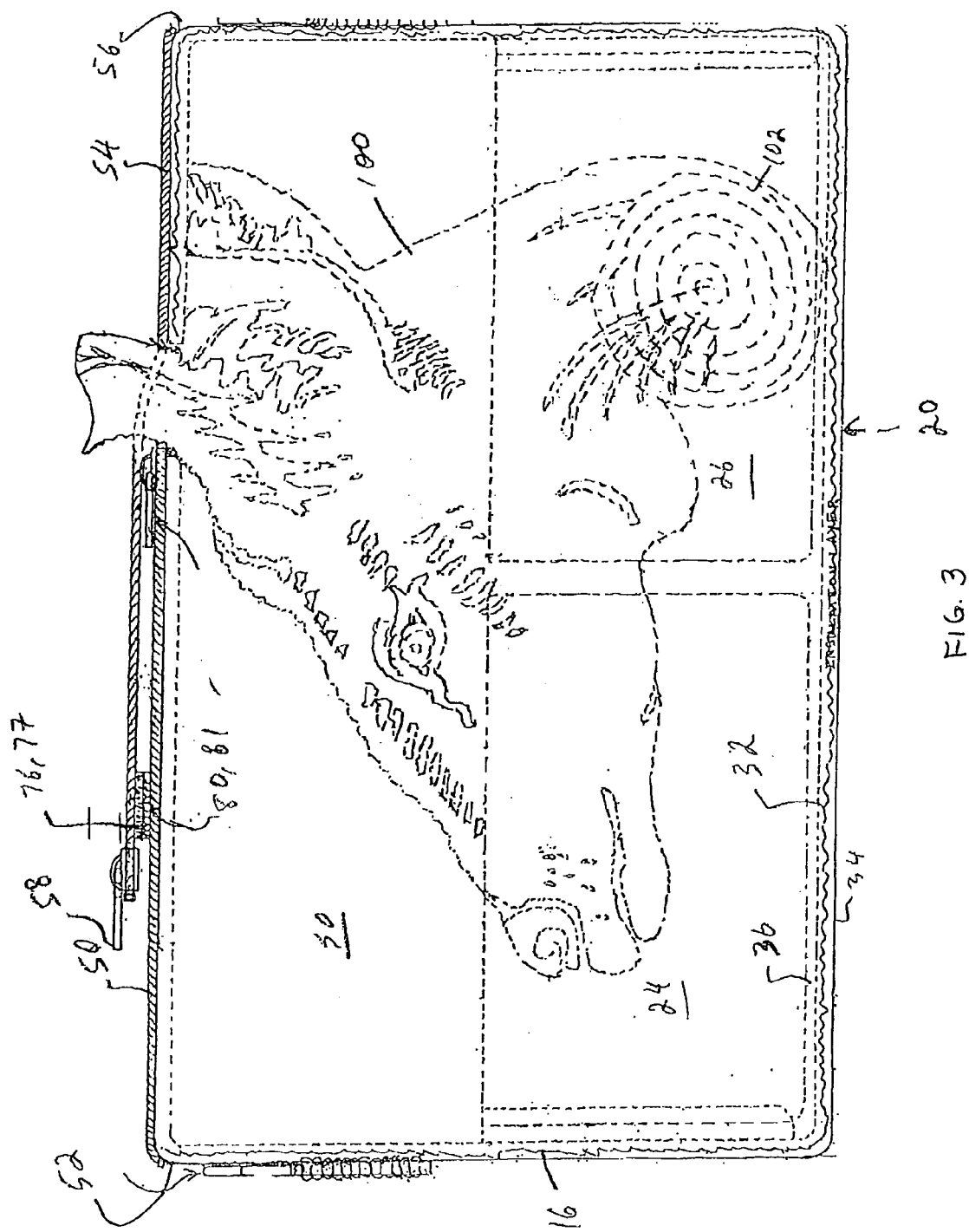
FIG. 3 is a cross sectional side view of the cooler showing the head and hide of the animal inside the main chamber.

The top 22 of the cooler 10 is provided with closing means for enclosing the main chamber 30. As can be seen in FIG. 3, the closing means comprises a first zipper 50, which extends along the center of the top 22, from one end 52 of the top 22 to about one-third of the top 22. The second zipper 54 extends through the center of the top 22, from the second end 56 to about two-thirds of the top 22, passing between the openings 60, 62 formed in the top 22. For some of its length, the second zipper 54 extends above the first zipper 50, thereby partially overlapping the first zipper 50.

Figure 10:
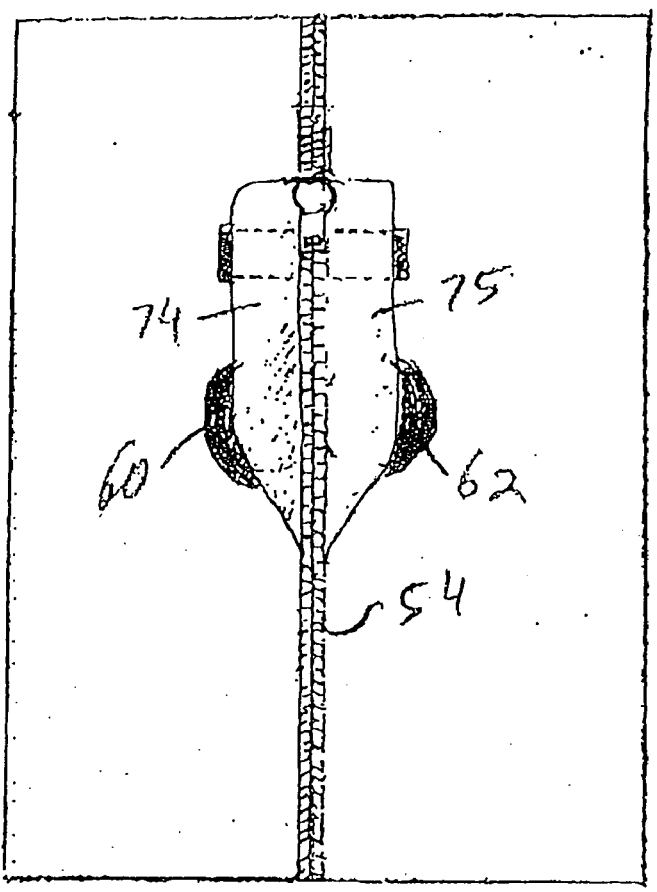
FIG. 10 is a detail top view of the cooler top showing openings for the antlers and a closing zipper.
Figure 11:
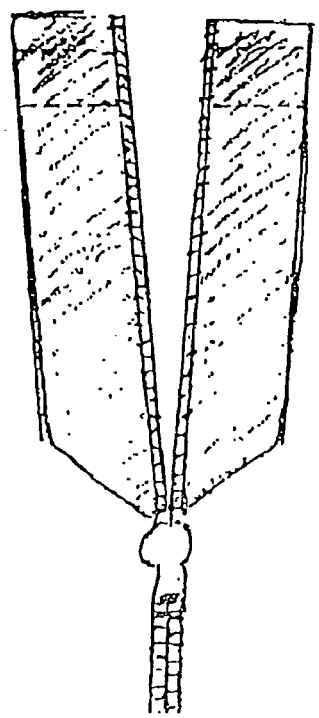
FIG. 11 is a side, partially cross-sectional view showing zippers and a closing flap surrounding the protruding antlers.

The first zipper 50 ends at a location adjacent to the openings 60, 62 formed in the top 22 (FIG. 10). The openings 60, 62 are configured to allow antlers of a deer to protrude outside of the cooler 10. The second zipper 54 ends at a point 58, which is at a distance from the openings 60, 62 and closer to the end wall 16, as can be seen in more detail in FIG. 3.

A cord-receiving pocket 64, 66 is formed about the openings 62, 64, respectively. A tightening cord 68, 70 is inserted in the respective pocket 64, 66 and extends from the pocket to facilitate tightening of the top 22 about the antlers 72, which protrude through the openings 60, 62 and protect the cool air created in the chamber 30. The openings 60, 62 can vary in size and are preferably large enough to accommodate different size antlers.

A pair of reinforcing members 74, 75 is secured to the top 22 by stitching and the like to reinforce the area adjacent the openings 60, 62. The zipper 54 passes between the reinforcing members 74, 75, as shown in more detail in FIG. 10. Each of the reinforcing members 74, 75 carries a hook-and-loop fastener strip 76, 77 secured to the underside of the respective flap adjacent end 78, 79 thereof. A matching hook-and-loop fastener strip 80, 81 is secured to the top 22 for engagement with the fastener strips 76, 77. When the strips 76, 77 and 80, 81 are engaged together, the pushing force of the deer head 100 positioned in the chamber 30 on the zippers 50, 54 is minimized by the securing strips engaging the top 22.

The cooler 10 of the present invention is provided with a carrying strap 86, which extends from the end wall 16 to the end wall 18. A securing ring 88 and 90 is positioned on the end walls 16 and 18, respectively, and secured with a respective ring support 92, 94. The carrying strap 86 carries a snap member 96 on each of its ends for detachably engaging the securing rings 88 and 90. The strap 86 can be dimensioned for carrying in hand, or across the shoulder, as desired.

In operation, a hunter prepares the hide of the animal and removes head from the carcass. The hide is then rolled up into a roll 102 and placed under the deer's neck, as shown in phantom lines in FIG. 3. The head 100 and the hide 102 are then placed into the chamber 30 of the cooler 10, with the nose of the dead animal facing one of the end walls 16. The antlers 72 are allowed to protrude through the openings 60, 62.

The user then place a cooling medium into the inner pockets 24, 26, 28 to maintain the head and carcass of the animal under the desired cool conditions. The zippers 50, 55 are then closed and the reinforcing flaps 74, 75 pressed in the area of hook-and-loop fasteners to engage the marching strips 80, 81. The tightening cords 68, 70 are tightened and tied to further protect the inside of the cooler.

The outside surface 34 of the cooler 10 may be camouflaged, if desired to match the clothing of the hunter. When not in use, the cooler 10 may be rolled up for storage and transportation.

Many changes and modifications may be made in the design of the present invention without departing from the spirit thereof. I, therefore, pray that my rights to the present invention be limited only by the scope of the appended claims.

We claim:

1. A portable container apparatus for retaining a head and cape of an animal, said apparatus comprising:
    a flexible deformable body defining an insulated chamber;
    a lid secured to upper peripheral edges of the body, said lid having a pair of hinged portions, a closing means extending between said hinged portions for enclosing the insulated chamber,
    and at least one opening is formed in said lid to allow a part of the animal to protrude therethrough, and wherein a tightening member is positioned around said opening to facilitate narrowing of said opening upon demand to conform to the size of said protruding animal part, and wherein said closing means comprises a first closing member extending from a first end of the lid, a second closing member extending from a second end of the lid and partially overlapping the first closing member, and a reinforcing flap secured to each of said lid portions for reinforcing parts of said lid portions adjoining said at least one opening.

2. The apparatus of claim 1, wherein a plurality of pouches are secured to interior walls of said body, said pouches being sized and shaped to receive cooling media therein.

3. The apparatus of claim 1, wherein at least one pocket is formed on an exterior wall of said body for retaining small items therein.

4. The apparatus of claim 1, further comprising a handle means detachably secured to said body to facilitate transportation of said body.

5. The apparatus of claim 4, wherein said handle means comprises an elongated strap extending between opposing end walls of said body and a securing member attached to a respective end wall of said body, said securing member being detachably engageable with said strap.

6. The apparatus of claim 1, wherein said body is formed from a flexible deformable waterproof insulated material.

7. A portable container apparatus for retaining a head and cape of an animal, said apparatus comprising:
    a flexible deformable body having a closed bottom, closable top and waterproof insulated walls defining an insulated chamber therebetween;
    a lid secured to upper peripheral edges of the body, said lid having a pair of hinged portions and a closing means extending between said hinged portions for enclosing the insulated chamber, said closing means comprising a first closing member extending from a first end of the lid and a second closing member extending from a second end of the lid and partially overlapping the first closing member, said first closing member and said second closing member extending substantially along a center of the lid, and wherein at least one opening is formed in said lid to allow a part of the animal to protrude therethrough, and wherein a tightening cord is positioned around said opening to facilitate narrowing of said opening upon demand to conform to the size of said protruding animal part, said lid has a pair of opposing portions and a reinforcing flap secured to each of said lid portions for reinforcing parts of said lid portions adjoining said at least one opening.

8. The apparatus of claim 7, wherein a plurality of pouches are secured on interior walls of said body, said pouches being sized and shaped to receive cooling media therein.

9. The apparatus of claim 7, wherein at least one pocket is formed on an exterior wall of said body for retaining small items therein.

10. The apparatus of claim 7, further comprising a handle means secured to said body to facilitate transportation of said body, said handle means comprising an elongated flexible strap extending between opposing side walls of said body.

* * * * *